United States Patent [19]

Osband et al.

[11] Patent Number: 4,716,111

[45] Date of Patent: Dec. 29, 1987

[54] PROCESS FOR PRODUCING HUMAN ANTIBODIES

[75] Inventors: Michal E. Osband, Brookline; Joy A. Cavagnaro, Boston, both of Mass.

[73] Assignee: Trustees of Boston University, Boston, Mass.

[21] Appl. No.: 696,546

[22] Filed: Jan. 30, 1985

Related U.S. Application Data

[63] Continuation of Ser. No. 407,236, Aug. 11, 1982, abandoned.

[51] Int. Cl.$^4$ .................... C12P 21/00; C12N 15/00; C12N 5/00
[52] U.S. Cl. .................. 435/68; 435/172.2; 435/240; 424/85
[58] Field of Search ............ 435/68, 172.2, 240; 424/85; 260/112 R, 112 B

[56] References Cited

U.S. PATENT DOCUMENTS 4,444,887   4/1984   Hoffmann .................... 435/240

OTHER PUBLICATIONS

Fauci, A., et al., J. Exp. Med., vol. 144, pp. 674–684, 1976.
Delfraissy, J., et al., J. Immunol., vol. 118, pp. 630–635, 1977.
Dosch, H., et al., J. Immunol., vol. 118, pp. 302–307, 1977.
Geha, R., et al., J. Exp. Med., vol. 138, pp. 1230–1247, 1973.
Chemical Abstracts, vol. 67, p. 10060, Abstract No. 106882n, 1967.
Chemical Abstracts, vol. 96, p. 530, Abstract No. 102175k, 1982.
Chemical Abstracts, vol. 96, Abstract No. 63191r, 1982.
Chemical Abstracts, vol. 96, p. 555, Abstract No. 21571a, 1982.
Chemical Abstracts, vol. 75, p. 101, Abstract No. 116802r, 1971.
Chemical Abstracts, vol. 95, p. 504, Abstract No. 201886d, 1981.
Chemical Abstracts, vol. 95, p. 492, Abstract No. 185412, 1981.
Chemical Abstracts, vol. 94, p. 28, Abstract No. 185467, 1981.
Steinitz et al., Nature, vol. 269, pp. 220–222, 1977.

*Primary Examiner*—Blondel Hazel
*Attorney, Agent, or Firm*—Paul J. Cook

[57] ABSTRACT

Human antibodies are provided by collecting the mononuclear cells from human blood, removing suppressor T-cells and exposing the remaining lymphocyte cells to an antigen, autologous serum of the human patient and a nonspecific lymphocyte activator.

6 Claims, No Drawings

PROCESS FOR PRODUCING HUMAN ANTIBODIES

BACKGROUND OF THE INVENTION

This is a continuation of application Ser. No. 407,236 filed Aug. 11, 1982 now abandoned.

This invention relates to a process for producing human antibodies utilizing human blood lymphocytes.

At the present time, antibodies are produced by injecting an antigen into a non-human animal, bleeding the animal and isolating the antibody from the blood serum. The use of xenogenic (cross-species) antibodies is of limited clinical value since there is an attendant risk of anaphylaxis or other allergic reactions.

An alternative method available at the present time involves the production of monoclonal antibodies from hybridomas. In these processes, an antigen is injected into a non-human animal followed by splenectomy. The immunized B cells of the spleen then are fused with myeloma cells. Unfortunately it is not possible to provide the technology used in the production of non-human animal monoclonal antibodies to the formation of human antibodies. Specifically, it is not feasible to inject an antigen into a person and subsequently remove their spleen for fusion with human myeloma cells. Furthermore, even if lymphocyte cells could be obtained from the patient in a safe manner, the type of anitgen that could be introduced into the human is quite limited, also due to safety reasons.

It would be highly desirable to provide a process for producing human antibodies by utilizing human lymphocytes obtained in a manner which does not produce a threat to the patient's health. Furthermore, it would be desirable to provide such a process wherein continuous cell lines can be formed so that the human antibody can be obtained continuously over a long period of time.

SUMMARY OF THE INVENTION

In accordance with this invention, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody.

DETAILED DESCRIPTION OF SPECIFIC EMBODIMENTS

In the process of this invention, blood is taken from a patient not previously exposed to the antigen which effects the production of the desired antibody. A portion of the sample is utilized to provide a source of autologous serum while the remainder of the sample is mixed with an anticoagulant such as heparin, sodium citrate, ethylenediaminetetraacetic acid, sodium oxalate or the like. The blood-anticoagulant mixture then is diluted in a physiologically acceptable solution such as sodium chloride or phosphate buffer solution. It is treated to recover the mononuclear cells by first layering the blood-anticoagulant composition in a centrifugation separation medium such as Ficoll-Hypaque obtained from Pharmacia Corporation of Lymphocyte Separation Medium obtained from Litton Bionetics Corporation. The resultant layered composition then is centrifuged and the interface containing the mononuclear cells is collected and washed.

The suppressor T-cells then are removed by contacting the mononuclear cells with an agent having a specific affinity for suppressor T-cells and not other T-cells or B-cells. A particularly suitable composition for depleting the mononuclear cells of suppressor T-cells is (1) an H2 receptor antagonist such as cimetidine, either linked or conjugated to a macromolecule such as human albumin and (2) an antibody directed against an antigen expressed on human suppressor T-cells such as OKT8, (Ortho) or Leu-2A (Becton-Dickinson). Utilizing human albumin linked to cimetidine provides the capability of removing only those cells bearing a histamine H2 type receptor on their surface so that the non-adherent cells are greatly enriched with B-cells. The mononuclear cells depleted of suppressor T-cells are suspended in a culture medium to which is added the antigen and the autologous serum and which contains a nonspecific lymphocyte activator.

Any antigen capable of eliciting the production of a specific antibody can be utilized in the present invention, including antigens which produce antibodies to drugs such as amphetamines or barbituates, antiviral antibodies, antibodies to human hormones or the like. The amount of antigen utilized will vary with the specific antigen and generally ranges between about 20 $\mu$g and about 1000 $\mu$g and can be lesser or greater in certain specific instances. It is to be understood that the amount of the antigen to be utilized can easily be determined through trial and error employing the techniques of this invention merely by measuring the quantity of antibody produced as a function of the amount of antigen utilized.

It is necessary to utilize autologous serum rather than serum obtained from another human or a non-human animal in accordance with this invention. It is believed that autologous serum will optimally activate the particular patient's B-cells to produce the desired antibody. The amount of autologous serum utilized can be between about 5 and about 25%.

In each culture medium, the concentration of mononuclear cells can be varied between about 0.5 and about $5.0 \times 10^6$ cells/ml in order to obtain optimum results with a concentration of about $2.0 \times 10^6$ cells/ml being most preferred. Any standard tissue culture medium can be utilized in the process of this invention including RPMI 1640 available from M. A. Bioproducts.

Representative suitable nonspecific lymphocyte activators include phytohemagglutinin (PHA), pokeweed mitogen (PWM), or a supernatant of a mixed lymphocyte culture (MLC) obtained by autologous cells against irradiated allogeneic cells. The supernatant of mixed lymphocyte culture contains, amongst many lymphokines, a molecule known as allogeneic effect factor (AEF). This mixed lymphocyte culture can be utilized in the final culture medium in an amount of between 10 and 50%, preferably between about 25 and 33%. The culture can be used immediately or stored frozen at −20° C. and then thawed for use. The duration that the mixed lymphocyte culture goes on prior to collecting the supernatant is about 48 hours, preferably between about 48 and about 60 hours. The optimal concentration of PHA and PWM can vary from lot to lot and manufacturer to manufacturer. Therefore, all that one needs to do is to test each lot and optimize each batch of material prior to utilizing it in volume.

The mononuclear cells then are tested for antibody production by any conventional means such as radioimmunoassay or the standard enzyme-linked immunosorbent assay (ELISA). In the ELISA, antigen first is adsorbed onto a plate and then washed. The supernant from the culture, which may or may not contain specific antibody, then is added to the plate and any specific antibody is attached to the antigen. The resultant antigen-antibody complex then is washed and an enzyme-labeled anti-antibody is added to the plate and it attaches to any antibody present. The resultant antigen-antibody-anti-antibody then is washed and a substrate for the enzyme is added. The amount of substrate degraded then is correlated to the amount of antibody present by means of a previously established standard curve. In the process for assaying for antibody produced by the present invention, it is convenient to define a positive test culture as one having a color change tht is at least two standard deviations greater than the mean of the control wells.

The lymphocyte cells producing antibody can be immortalized by any conventional means such as by exposure to Epstein-Barr virus or by fusion to myeloma cells by the procedure of Köhler and Milstein.

The following example illustrates the present invention and is not intended to limit the same.

EXAMPLE I

This example illustrates the process of this invention for producing human antibodies in vitro. The following compositions were prepared:

Culture medium A

RPMI 1640 containing 7.5% fetal calf serum (v/v).

Culture medium B

RPMI 1640 medium (56.7% v/v).

Autologous serum (10% v/v) was obtained from a previous venipuncture heat-inactivated at 56° C. for 30 minutes and stored at −20° C. until use. Supernatant from a mixed lymphocyte culture (see below) (33.3%) was produced. In addition, the culture medium B is supplemented with: Hepes buffer 0.025M, glutamine 0.002M, penicillin (50 units/ml) and streptomycin (50 ug/ml).

Culture medium C

RPMI 1640 containing 95% (v/v medium), 5% autologous serum (v/v) and supplemented as in B above.

Production of Mixed Lymphocyte Culture Supernatant

1. Autologous peripheral blood mononuclear cells were obtained as set forth above.
2. They are resuspended in culture medium C at $2 \times 10^6$ cells/ml.
3. Allogeneic peripheral blood mononuclear cells were obtained, resuspended at $10 \times 10^6$ cells/ml in culture medium C and irradiated with 3000 rad. Following irradiation the allogeneic cells are diluted with culture medium B to a concentration of $2 \times 10^6$ cells/ml.
4. Responder (autologous to the immunization donor) and stimulator (the allogeneic source) cell suspensions are mixed 1:1 vol.
5. The final cell suspension ($2 \times 10^6$ cells/ml composed of $1 \times 10^6$ cells stimulator and $1 \times 10^6$ cells/ml responder cells) was cultured for 48 hours at 37° C. in a moist-air incubator containing 5% $CO_2$.
6. At 48 hours, the culture is centrifuged to pellet the cells and the supernatant used immediately or frozen at −20° C. until thawed and used.

The following represents the process used to immunize primarily in vitro human cells against rabbit immunoglobulin.

1. 100 cc of peripheral venous blood was collected in preservative-free heparin from a healthy adult donor.
2. The blood was diluted 1:1 with normal saline and layered on Lymphocyte Separation Medium (2:1 blood mixture to LSM), centrifuged at 800×g for 20 minutes at room temperature.
3. The interface cells were collected and washed ×2 with Hank's Balanced Salt Solution.
4. The pellet was resuspended in culture medium A at $7 \times 10^6$ cells/ml, layered onto a HAC-coated petri dish and incubated at 37° C. for 60'. At that time, the petri dish was swirled gently and the medium poured off. The plate was washed ×1 by swirling gently with 10 ml of culture medium A and poured off. These two pour-offs contain the histamine H2 receptor depleted (suppressor T-cell) population. These cells were washed ×2 in HBSS and resuspended in culture medium B to which was added rabbit immunoglobulin to a final concentration of 800 ug/ml. This plate and technique for the depletion of histamine H2 receptor bearing suppressor T-cells is the topic of another patent application.
5. The cells were cultured at 37° C. in a moist-air incubator with 5% $CO_2$ at a density of $1 \times 10^6$ cells/ml.
6. After 7 days, the supernatants were screened for the presence of anti-RIG antibody by standard ELISA technique. The supernatants from these cultures were positive in that they had reactivity that was at least 2 standard deviations greater than that found in the supernatants from control wells (wells with antigen and only 1 parameter).

We claim:

1. A process for producing a human antibody which comprises collecting mononuclear cells depleted of suppressor cells from the autologous blood of a human patient not previously exposed to an antigen which elicits and human antibody, adding to said mononuclear cells an antigen capable of initiating the production of said human antibody, adding to said mononuclear cells autologous serum from said patient and incubating said mononuclear cells, antigen and autologous serum in the presence of a non-specific lymphocyte activator for a period of time sufficient to effect the production of a human antibody.

2. The process of claim 1 wherein said activator is phytohemagglutinin.

3. The process of claim 1 wherein said activator is pokeweed mitogen.

4. The process of claim 1 wherein said activator is a supernatant of a mixed lymphocyte culture containing allogenic effect factor.

5. The process of any one of claims 1, 3 or 4 wherein the cells producing desired antibody said mononuclear cells are immortalized.

6. The process of any one of claims 1, 3 or 4 wherein the cells producing desired antibody said mononuclear cells are immortalized by being fused with myeloma cells.

* * * * *

UNITED STATES PATENT AND TRADEMARK OFFICE
CERTIFICATE OF CORRECTION

PATENT NO. : 4,716,111

DATED : December 29, 1987

INVENTOR(S) : Michael E. Osband and Joy A. Cavagnaro

It is certified that error appears in the above-identified patent and that said Letters Patent is hereby corrected as shown below:

Claim 1, Line 5 after "elicits" replace "and" with -- said --.

Signed and Sealed this

Twenty-ninth Day of November, 1988

Attest:

DONALD J. QUIGG

Attesting Officer

Commissioner of Patents and Trademarks